United States Patent
Huang et al.

(10) Patent No.: US 8,439,858 B2
(45) Date of Patent: May 14, 2013

(54) ARTERIAL BLOOD FILTER

(75) Inventors: Trevor C. Huang, Maple Grove, MN (US); Alford L. McLevish, Maple Grove, MN (US); Joseph L. Kalscheuer, Minneapolis, MN (US); Roderick E. Briscoe, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 752 days.

(21) Appl. No.: 11/948,290

(22) Filed: Nov. 30, 2007

(65) Prior Publication Data

US 2009/0105630 A1    Apr. 23, 2009

Related U.S. Application Data

(60) Provisional application No. 60/980,609, filed on Oct. 17, 2007.

(51) Int. Cl.
*A61M 39/00* (2006.01)
*A61M 37/00* (2006.01)
*B01D 36/00* (2006.01)
*A61M 1/34* (2006.01)
*A61M 1/36* (2006.01)

(52) U.S. Cl.
USPC ....... 604/6.09; 604/4.01; 604/5.01; 604/6.14; 604/6.15; 210/304; 210/294; 210/295; 210/321.6; 422/44

(58) Field of Classification Search ........ 604/5.01, 604/6.09, 6.15, 6.16, 93.01, 4.01, 6.14; 422/44; 210/512.3, 304, 294, 295, 321.6, 321.62, 210/321.72, 321.76, 321.77, 321.78, 321.84, 210/321.85, 321.86; 600/16
See application file for complete search history.

(56) References Cited

U.S. PATENT DOCUMENTS

| | | | | |
|---|---|---|---|---|
| 3,849,071 A | * | 11/1974 | Kayser | 422/45 |
| 4,035,304 A | | 7/1977 | Watanabe | |
| 4,157,965 A | * | 6/1979 | Raible | 210/305 |

(Continued)

FOREIGN PATENT DOCUMENTS

| | | |
|---|---|---|
| EP | 1 084 722 | 3/2001 |
| JP | 01148266 | 9/1989 |
| WO | 96/33770 | 10/1996 |
| WO | 2006/128628 | 12/2006 |

OTHER PUBLICATIONS

Online encyclopedia article "Tangent" accessed Jun. 23, 2010. http://en.wikipedia.org/wiki/Secant_line.*

(Continued)

*Primary Examiner* — Leslie Deak
*Assistant Examiner* — Adam Marcetich

(57) ABSTRACT

An arterial line blood filter for use in extracorporeal blood circuits during heart bypass surgery has, among other components, a housing with a cap portion, a base portion, and a generally cylindrical wall portion. The blood filter has a filter element disposed within the housing. An inlet is positioned at an upward angle with respect to the housing and includes an opening in the generally cylindrical wall portion in fluid communication with the inlet chamber. In some embodiments the position of the inlet limits the pressure drop and prime volume of the filter. According to one embodiment, the cap portion has an upwardly sloping inner surface and there is a vent in the cap portion. The inner surface of the cap portion can have a projection proximate the vent configured to limit immobilization of gaseous microemboli within the inlet chamber.

19 Claims, 11 Drawing Sheets

U.S. PATENT DOCUMENTS

| | | | |
|---|---|---|---|
| 4,304,670 A | | 12/1981 | Watanabe et al. |
| 4,336,224 A | | 6/1982 | Siposs |
| 4,411,783 A | | 10/1983 | Dickens et al. |
| 4,422,939 A | | 12/1983 | Sharp et al. |
| 4,490,254 A | | 12/1984 | Gordon et al. |
| 4,655,740 A | * | 4/1987 | Ruhland ................ 604/6.09 |
| 4,678,566 A | | 7/1987 | Watanabe et al. |
| 4,690,762 A | * | 9/1987 | Katsura ................ 96/212 |
| RE32,711 E | | 7/1988 | Dickens et al. |
| 4,774,019 A | | 9/1988 | Watanabe et al. |
| D299,269 S | | 1/1989 | Pierson et al. |
| 4,806,135 A | | 2/1989 | Siposs |
| 4,919,802 A | | 4/1990 | Katsura |
| 4,932,987 A | | 6/1990 | Molina |
| 4,964,984 A | * | 10/1990 | Reeder et al. ................ 210/188 |
| D317,201 S | | 5/1991 | Sone |
| 5,039,430 A | | 8/1991 | Corey et al. |
| 5,203,999 A | | 4/1993 | Hugues |
| 5,282,783 A | * | 2/1994 | Lindsay ................ 604/6.09 |
| 5,312,479 A | | 5/1994 | Weinstein et al. |
| D355,973 S | | 2/1995 | Ijiri et al. |
| 5,484,474 A | | 1/1996 | Weinstein et al. |
| 5,547,576 A | | 8/1996 | Onishi et al. |
| 5,618,425 A | | 4/1997 | Mitamura et al. |
| 5,632,894 A | | 5/1997 | White et al. |
| 5,651,765 A | | 7/1997 | Haworth et al. |
| 5,782,791 A | | 7/1998 | Peterson et al. |
| 5,849,065 A | | 12/1998 | Wojke |
| 6,051,134 A | * | 4/2000 | Schnell et al. ................ 210/188 |
| 6,176,904 B1 | | 1/2001 | Gupta |
| 6,267,926 B1 | | 7/2001 | Reed et al. |
| 6,312,414 B1 | | 11/2001 | Brockhoff et al. |
| 6,398,955 B1 | | 6/2002 | Fumiyama |
| 6,451,257 B1 | | 9/2002 | Flamer |
| 6,682,698 B2 | | 1/2004 | Chambers et al. |
| 6,723,283 B2 | | 4/2004 | Ghelli et al. |
| 7,025,056 B2 | | 4/2006 | Eason et al. |
| 7,147,614 B2 | * | 12/2006 | Fini ................ 604/6.15 |
| 2006/0015056 A1 | | 1/2006 | Ellingboe et al. |
| 2006/0167400 A1 | | 7/2006 | Ellingboe et al. |
| 2006/0191841 A1 | | 8/2006 | Kawarabata et al. |
| 2007/0293805 A1 | * | 12/2007 | Ghelli et al. ................ 604/6.15 |

OTHER PUBLICATIONS

PCT International Search Report, International Appl. No. PCT/US2008/079325, mailing date Apr. 21, 2009 (6 pages).

* cited by examiner

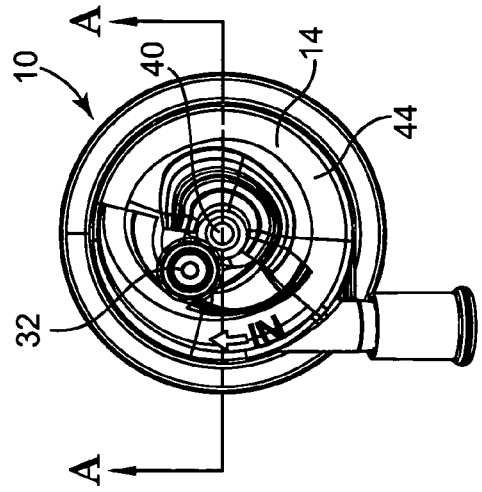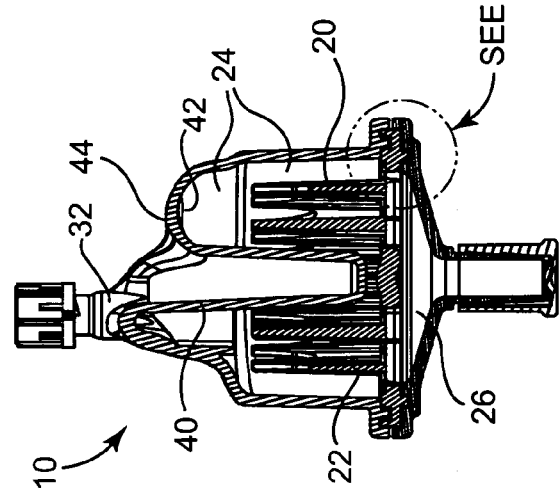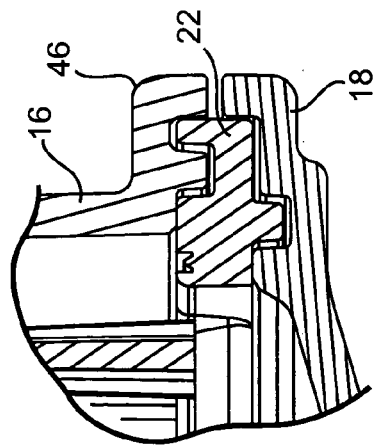

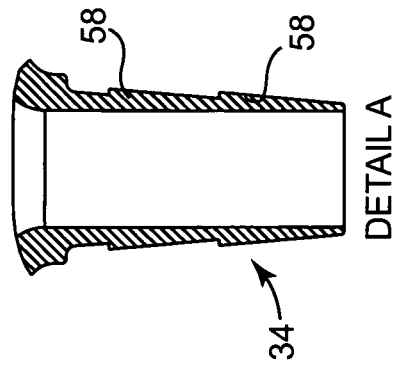
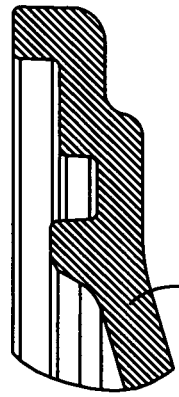
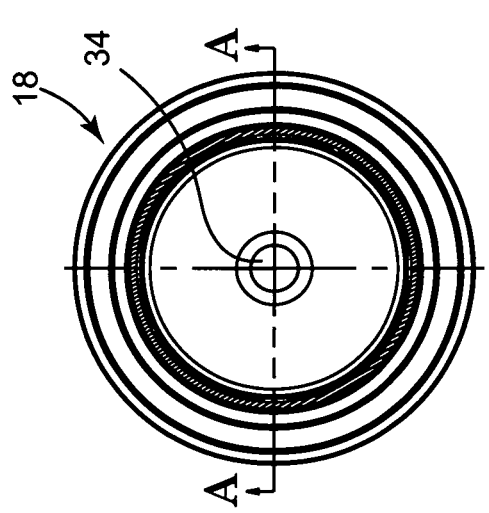
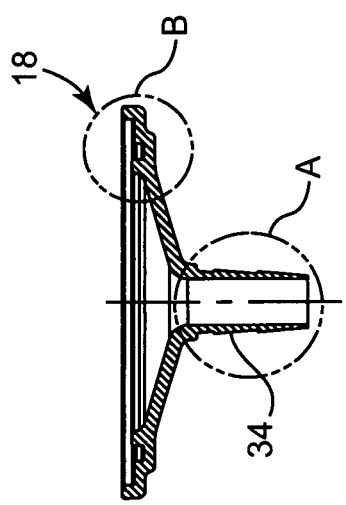

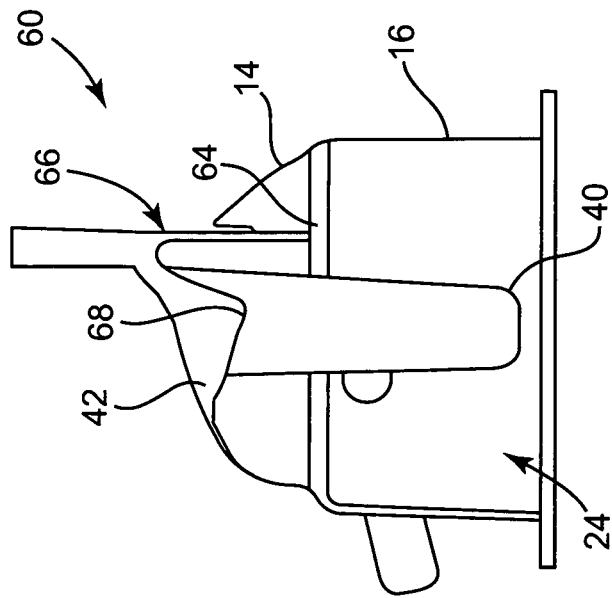
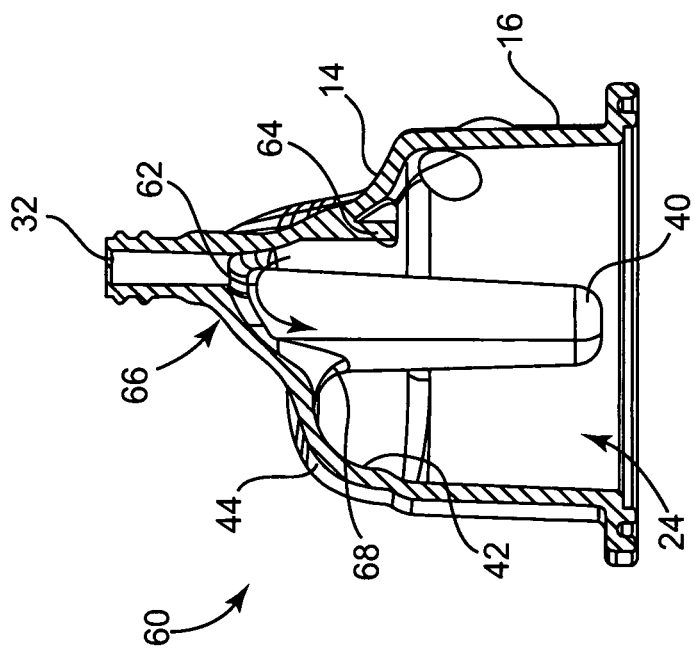

SECTION D-D

# US 8,439,858 B2

ARTERIAL BLOOD FILTER

CROSS-REFERENCES

This application claims the benefit of U.S. Provisional Application No. 60/980,609, titled "Arterial Blood Filter," filed Oct. 17, 2007, the entire contents of which are hereby incorporated by reference.

FIELD

Embodiments of the invention generally relate to blood filters used in extra corporeal blood circuits. More particularly, the embodiments of the invention relate to an arterial line blood filter used to filter blood during cardiovascular surgery.

BACKGROUND

An arterial line blood filter device or "arterial filter" or "blood filter" is one component of an extracorporeal blood circuit, which is used, for example, during cardiopulmonary bypass procedures. The arterial filter removes microscopic sized particles, e.g., microemboli, suspended in oxygenated blood before it re-enters the patient's body. This embolic material has the potential to cause health problems if returned to the patient, and includes (i) particulate matter, such as platelet or white cell aggregates, fat, clots and other foreign matter; and/or (ii) gaseous matter, such as small or large gas (e.g., air) bubbles. Particulate emboli are retained in an arterial filter because their particle size is excluded by the filter's pore size, thereby trapping the emboli and preventing them from continuing in the blood flow into the patient's body. Once the filter has been primed or wetted, fluid covers the filter pores and blocks gaseous microemboli from passing through the pores. Additionally, the gaseous microemboli are cleared from the filter through a vent port in the cap of the filter.

U.S. Pat. No. 5,651,765 discloses one example of an arterial filter. The arterial filter has a housing with a cap portion, a base portion and a generally cylindrical wall portion. The filter element of the arterial filter is disposed within the housing and divides the housing into an inlet chamber in flow communication with a blood inlet and an outlet chamber in flow communication with a blood outlet. The filter element includes a plurality of concentric annular folds, the lengths of which are substantially equal to the length of the wall portion, the folds being supported by a support element. The inner surface of the cap defines an inwardly spiral blood flow path which slopes upward to facilitate removal of gaseous microemboli through a vent port.

In addition to adequately removing embolic material, the priming volume and the pressure drop associated with an arterial filter are also of interest. Arterial filters are generally "primed" before use in order to remove all gaseous matter within the filter. For example, a liquid, such as an isotonic solution, is often introduced into the filter to displace the gaseous matter initially present in the filter. The "prime" volume or "priming" volume of the filter refers to the volume of liquid needed to prime the filter. At the beginning of use, the solution within the filter is displaced by blood, and the solution mixes downstream with the blood. Accordingly, it is desirable to reduce the priming volume of the arterial filter in order to limit the amount of priming solution needed and to limit dilution of the blood before it re-enters the patient. This is especially desirable for arterial filters designed for use with pediatric patients, as the lower overall volume of blood leads to higher dilution than for an adult patient.

As is known, it is also desirable to reduce the pressure drop across the arterial filter in order to prevent hemolysis or other blood trauma. In order to maintain adequate pressure as the blood passes through various components of the extracorporeal blood circuit, a large initial pressure can be required to counteract pressure drops across one or more components. Increasing the overall pressure can lead to blood trauma, for example, as the blood encounters resistance throughout the circuit or from an elevated level of heat generated by the pressurizing pump. In addition, when decreasing the priming volume of an arterial filter, such as for a pediatric arterial filter, it is often also desirable to maintain an elevated flow rate through the filter, which can lead to further efforts to reduce the pressure drop across the arterial filter.

SUMMARY

According to one aspect of the invention, in some embodiments, an arterial line blood filter is provided, having, among other components, a housing with a cap portion, a base portion, and a generally cylindrical wall portion. A filter element is disposed within the housing and divides the housing into an inlet chamber and an outlet chamber. The filter element is supported by a support element fixedly connected to the housing. An inlet is positioned at an upward angle with respect to the housing and includes an opening in the generally cylindrical wall portion in fluid communication with the inlet chamber. An outlet in fluid communication with the outlet chamber provides a return path for the blood flow.

According to another aspect of the invention, in some embodiments, an arterial line blood filter is provided, having, among other components, a housing with a base portion, a generally cylindrical wall portion, and a cap portion having an upwardly sloping inner surface. A filter element is disposed within the housing and divides the housing into an inlet chamber and an outlet chamber. The filter element is supported by a support element fixedly connected to the housing. An inlet can be provided in fluid communication with the inlet chamber and an outlet can be provided in fluid communication with the outlet chamber to provide a return path for the blood flow. In some embodiments the cap portion also includes a vent and the upwardly sloping inner surface of the cap portion has a projection proximate the vent. The projection can be configured to limit the immobilization of gaseous microemboli within the inlet chamber.

According to another aspect of the invention, in some embodiments, an arterial line blood filter is provided, having, among other components, a cap portion, a base portion, and a generally cylindrical wall portion between the cap portion and the base portion. A filter element is disposed within the housing and divides the housing into an inlet chamber and an outlet chamber. The filter element is supported by a support element fixedly connected to the housing. The filter can include an inlet having an opening in the generally cylindrical wall portion such that the inlet is coupled to the wall portion in a non-tangential orientation. The filter also includes an outlet in fluid communication with the outlet chamber.

According to another aspect of the invention, a method of filtering arterial blood according to some embodiments includes providing a blood filter having a housing including a cap portion, a base portion, and a generally cylindrical wall portion between the cap portion and the base portion. The filter also has a filter element disposed within the housing, that divides the housing into an inlet chamber and an outlet chamber. A support element is fixedly connected to the housing for supporting the filter element and an inlet including an opening in the generally cylindrical wall portion is positioned at an upward angle with respect to the housing. The inlet opening is in fluid communication with the inlet chamber and an outlet is in fluid communication with the outlet chamber. The method further includes priming the blood filter and connecting the blood filter to a patient's circulatory system.

According to another aspect of the invention, a method of filtering arterial blood according to some embodiments includes providing a blood filter having a housing including a cap portion with an upwardly sloping inner surface, a base portion, and a generally cylindrical wall portion between the cap portion and the base portion. The filter also has a filter element disposed within the housing, that divides the housing into an inlet chamber and an outlet chamber. A support element is fixedly connected to the housing for supporting the filter element and an inlet is in fluid communication with the inlet chamber. The filter further includes a vent in the cap portion, and the upwardly sloping inner surface of the cap portion includes a projection proximate the vent configured to limit immobilization of gaseous microemboli within the inlet chamber. An outlet is in fluid communication with the outlet chamber. The method further includes priming the blood filter and connecting the blood filter to a patient's circulatory system.

BRIEF DESCRIPTION OF THE DRAWINGS

FIG. 3A is a side elevation view of an arterial filter according to an embodiment of the present invention.

FIG. 3B is a top view of the arterial filter of FIG. 3A.

FIG. 3C is a cross-sectional view of the arterial filter of FIG. 3B along line AA.

FIG. 3D is a detailed view of the coupling of components of the arterial filter of FIG. 3C.

FIG. 6A is a top view of a base portion of an arterial filter according to an embodiment of the present invention.

FIG. 6B is a cross-sectional view of the base portion of FIG. 6A along line AA.

FIG. 6C is a detailed view of an outlet of the base portion of FIG. 6B.

FIG. 6D is a detailed view of an edge of the base portion of FIG. 6B.

FIG. 8A is a partial cross-sectional, partial perspective view of the top portion of FIG. 7A according to an embodiment of the present invention.

FIG. 8B is a partial cross-sectional, partial perspective view of the top portion of FIG. 7A according to an embodiment of the present invention.

DETAILED DESCRIPTION OF THE PREFERRED EMBODIMENTS

Figure 1:
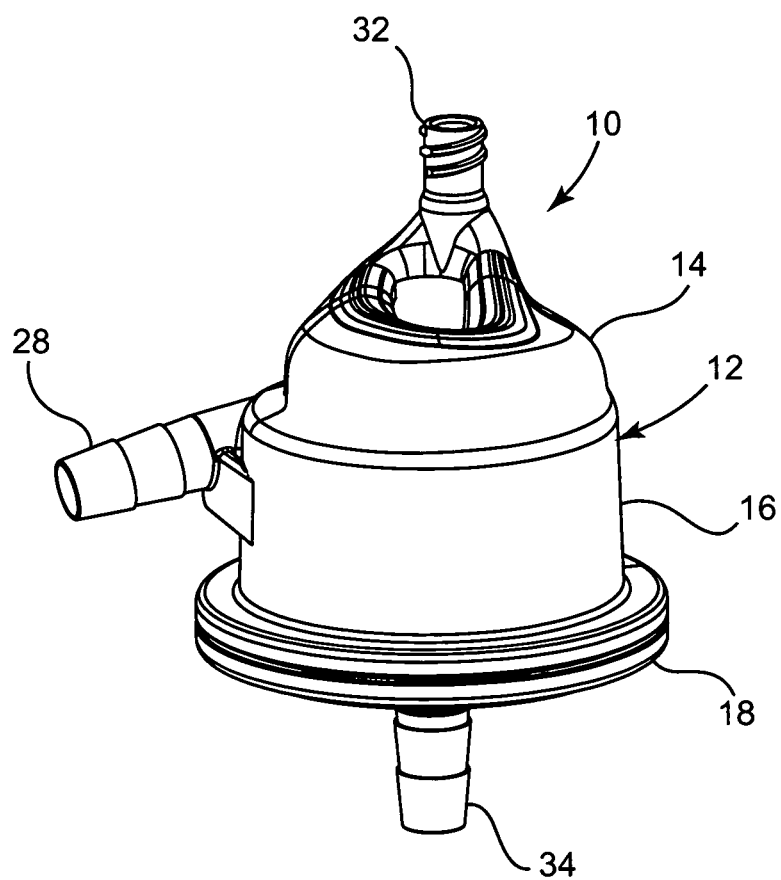
FIG. 1 is perspective view of an arterial filter according to an embodiment of the present invention.

The following detailed description should be read with reference to the drawings, in which like elements in different drawings are numbered identically. It will be understood that embodiments shown in the drawings and described herein are merely for illustrative purposes and are not intended to limit the invention to any embodiment. On the contrary, it is intended to cover alternatives, modifications, and equivalents as may be included within the scope of the invention as defined by the appended claims.

Figure 2:
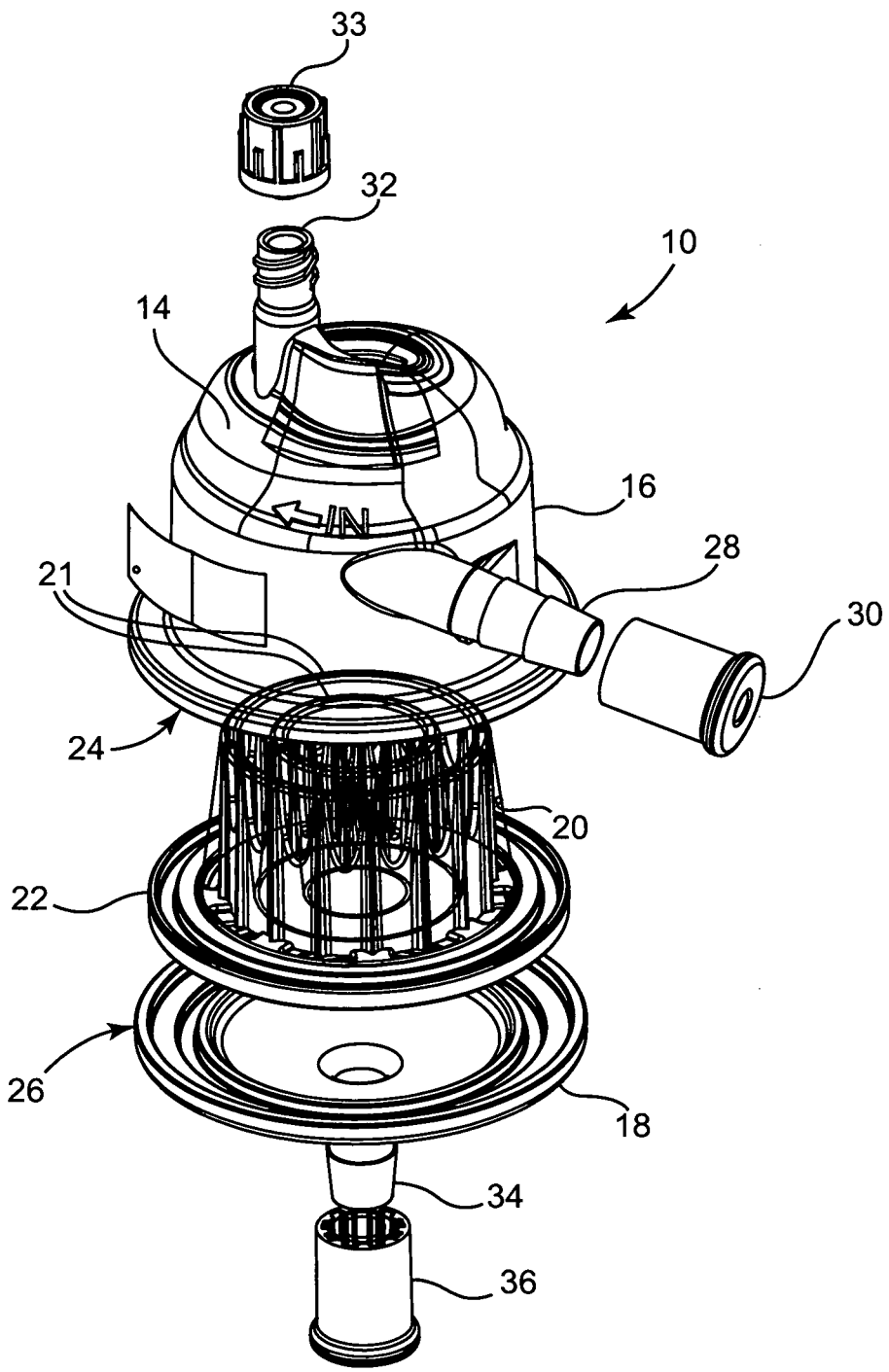
FIG. 2 is an exploded perspective view of the arterial filter shown in FIG. 1.

FIGS. 1 and 2 are perspective and exploded views, respectively, of an arterial blood filter 10 according to embodiments of the present invention. Blood filter 10 has a housing 12 which includes a cap portion 14, a generally cylindrical wall portion 16 and a base portion 18. The housing 12 encloses a filter element 20 having a plurality of concentric pleats 21. The filter element 20 is supported by a support element 22 and separates the interior of the housing 12 into an inlet chamber 24 and an outlet chamber 26. The cap portion 14, the wall portion 16 and the base portion 18 may be formed from separate pieces and coupled together. Alternatively, the wall portion 16 may be constructed as an integral piece with either the cap portion 14 or the base portion 18. In the embodiments shown throughout the Figures, the cap portion 14 is integral with the wall portion 16. The housing 12 can be made of a transparent medical grade material, such as a transparent polycarbonate, so that the user is able to observe the flow of blood through the device. Injection molding or other suitable processes known to those of skill in the art can be used to manufacture the pieces.

Further referring to the embodiments depicted in FIGS. 1 and 2, an inlet 28 is coupled to the wall portion 16 of the housing 12 and is in fluid communication with the inlet chamber 24. The inlet 28 may be connected to a line from an oxygenator (not shown) for receiving oxygenated blood or may be stopped by an inlet cap 30. In the embodiments shown throughout the Figures, the inlet 28 is formed as an integral portion of wall portion 16. As will be discussed in further detail hereinafter, the inlet 28 is angled upward with respect to the housing 12 and is spaced apart from the cap portion 14 according to one embodiment of the invention.

According to one embodiment, blood circulating through the inlet chamber 24 is directed towards the cap portion 14 in an inwardly spiral path as will be discussed in more detail hereinafter. A vent 32 is located at or near the top of the cap portion 14 and in some embodiments may be offset from a longitudinal axis of the filter. The vent 32 provides a means of venting gaseous microemboli from the blood filter 10, which rise to the top of the cap portion 14. In one embodiment the vent 32 is located at the highest point of the cap portion 14 to allow rising gaseous microemboli to escape from the blood filter. An optional vent cap 33 can prevent contaminants from entering the inlet chamber through the vent 32. Upon passing through the filter element 20, the blood passes through the outlet chamber 26 and through an outlet 34 located at the bottom of the base portion 18. The outlet 34 can be stopped with an outlet cap 36 when not in use, or connected to a patient return line (not shown) for providing oxygenated blood back to the patient.

In some embodiments, the blood filter 10 is configured for use with pediatric or infant patients. To avoid a large prime volume relative to the size of the patient, the blood filter has a reduced prime volume when compared with a conventional adult-sized arterial blood filter. For example, the prime volume may be up to five times smaller than a comparable adult-sized filter. In one embodiment the blood filter 10 measures approximately 2.1 inches in diameter and 3.4 inches in height and has a prime volume of 40 mL. While it is preferable in some embodiments to minimize the prime volume of the filter, especially for pediatric- or infant-compatible filters, the prime volume may vary according to particular designs. For example, in some embodiments, the filter may have a prime volume from as low as about 15 mL to as great as about 100 mL, although embodiments of the invention are not limited to this range.

While the prime volume may be significantly reduced, in some cases it may be desirable to have a disproportionately reduced flow rate through the blood filter, such as for pediatric filters. For example, blood trauma requirements may dictate a particular flow rate, while the filter prime volume can be more freely adjusted as long as flow rate and pressure drop requirements are satisfied. In one example, the prime volume may be about five times smaller, while the flow rate may only be reduced to about half of a normal flow rate for an adult-configured filter. In one embodiment, the blood filter 10 is capable of processing about 40 mL of blood at about 3.2 L/minute. These disproportionate characteristics can in some cases create a greater than desired pressure drop across the blood filter, which embodiments of the invention address as will be explained in further detail hereinafter.

Referring now to FIGS. 3A-3D, various views are shown of the assembled blood filter 10 depicted in the embodiment in FIG. 2. FIG. 3A shows a side elevation view of the assembled blood filter 10, while FIG. 3B shows a top view of the blood filter 10. FIG. 3C shows a cross-sectional view of the blood filter 10 along the line AA shown in FIG. 3B. According to this embodiment, the housing 12 comprises a volume displacer 40 around which the blood swirls, thus advantageously decreasing the priming volume of the blood filter 10. The volume displacer 40 can generally be described as a tube, which extends through the center of the inlet chamber 24 from the cap portion 14 towards the base portion 18. It may be formed as an integral part of the cap portion 14, as shown, or it may be a separate piece which is bonded to the cap portion 14. According to some embodiments, the volume displacer 40 extends into a center of the filter element 20 and the support element 22.

According to this embodiment, the vent 32 is offset from the opening of the volume displacer 40 in the cap portion 14. The cap portion 14 includes an inner surface 42 and an outer surface 44, which in one embodiment are generally shaped alike. As shown in FIGS. 3A-3C, the inner and outer surfaces 42, 44 of the cap portion 14 are contoured so as to generally spiral up and around the volume displacer 40, reaching a high point at the vent 32. The contour of the cap portion 14 guides at least some of the blood in the inlet chamber 24 up and around the volume displacer 40 in an inwardly spiraling blood flow path. The at least partially upward flow of blood helps to carry any gaseous microemboli past the vent 32 for venting out of the blood.

FIG. 3D shows a detailed view of a portion of FIG. 3C, illustrating one method of coupling the wall portion 16, the base portion 18, and the support element 22. As shown in FIG. 3D, the wall portion 16 includes a coupling flange 46. The coupling flange 46, the support element 22 and the base portion 18 include complimentary teeth or protrusions and grooves to enable a complimentary tongue-and-groove coupling configuration. The coupling can be set with an adhesive, thus providing a secure and airtight seal, although other suitable fasteners may also be used. For example, in one embodiment the coupling is set using ultrasonic welding techniques.

Figure 4C:
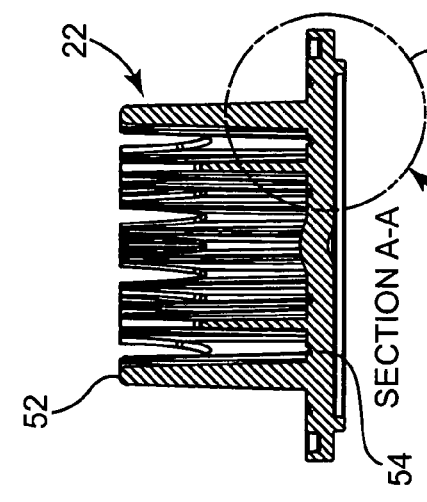
FIG. 4C is a cross-sectional view of the support element of FIG. 4B along the line AA.
Figure 4B:
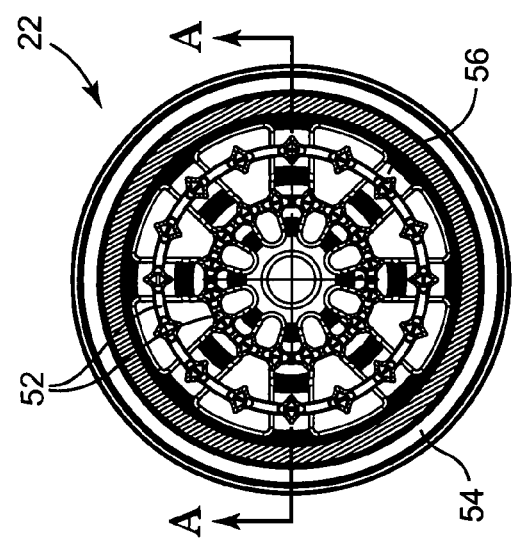
FIG. 4B is a bottom view of the support element of FIG. 4A.
Figure 4E:
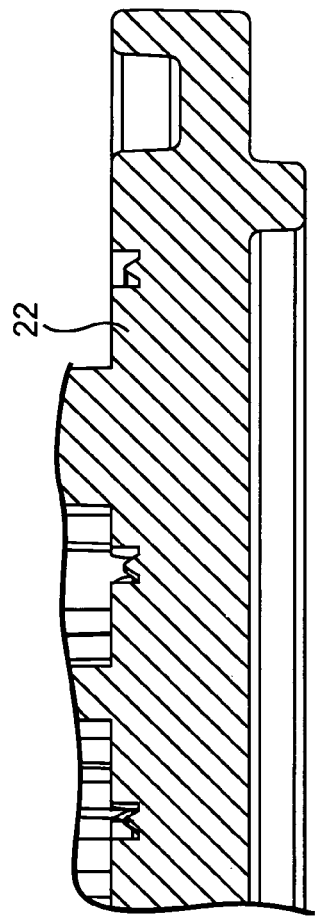
FIG. 4E is a detailed view of the support element of FIG. 4C.
Figure 4A:
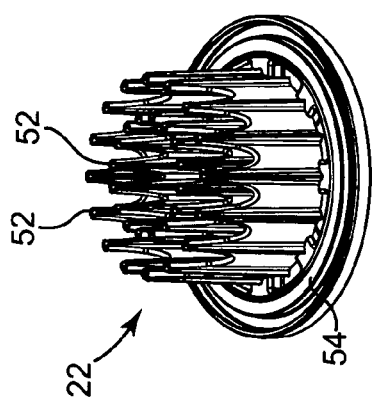
FIG. 4A is a perspective view of a support element according to an embodiment of the present invention.
Figure 4D:
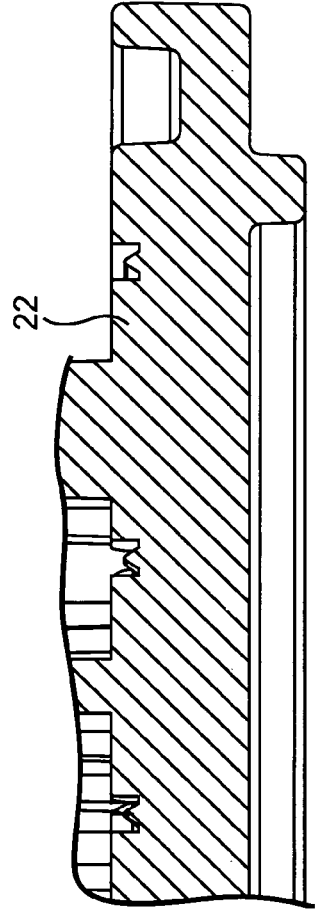
FIG. 4D is a cross-sectional view of the support element of FIG. 4B along the line BB.

FIGS. 4A-4E illustrate various views of the support element 22. As shown best in FIGS. 2 and 3C, the support element 22 is positioned within the housing 12 to provide support for the filter element 20. Generally, any manner of support which results in stabilizing the filter element 20 may be used and the invention is not intended to be limited to the illustrated embodiment. FIG. 4A is a perspective view of the support element 22 according to an embodiment of the present invention, FIG. 4B is a bottom view of the support element of FIG. 4A, FIG. 4C is a cross-sectional view of the support element of FIG. 4B along the line AA, FIG. 4D is a cross-sectional view of the support element of FIG. 4B along the line BB, and FIG. 4E is a detailed view of the support element of FIG. 4C.

The support element 22 includes a plurality of concentric annular members 52 with increasing diameters from the center of the support element, which nest within the concentric pleats 21 of the filter element 20. A base 54 supports a network of spokes 56 from which the annular members 52 project. As shown in FIG. 4B, the annular members 52 are generally concentric to a longitudinal axis of the blood filter 10 and spaced apart from the surrounding wall portion 16 and each other to leave sufficient space for blood to flow down and through the filter element 20. Each of the components may be made separately and then bonded together in a conventional manner to form support element 22. In one embodiment, the support element 22 is molded from a medical grade plastic as a single integral piece which is bonded in a conventional manner to base portion 18. Alternatively, the support element 22 may be formed as an integral portion of base portion 18. Advantageously, the blood filter of the present invention does not include a filter cap disposed on or over the filter element 20.

Figure 5:
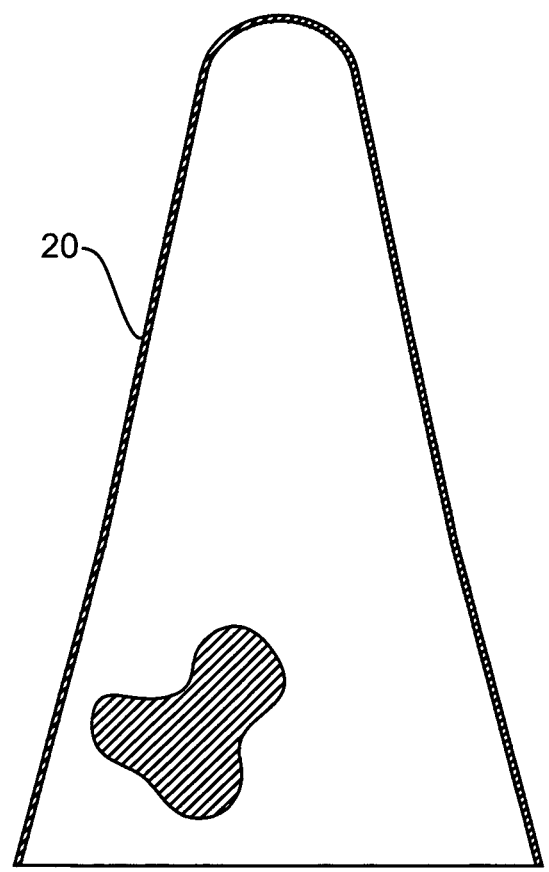
FIG. 5 illustrates a filter element according to an embodiment of the present invention.

FIG. 5 illustrates a cross-section of a possible design of the filter element 20 according to one embodiment. As one example, the filter element 20 can be similar in many respects to the filter taught by Peterson and Olsen in U.S. Pat. No. 5,782,791, the contents of which are herein incorporated by reference. The filter element is built in the form of a cone as shown by attaching two layers of filter material to each other at their edges. This forms the filter element 20, which is then concentrically folded over the annular members 52 of the support element and attached to the base 54 and spokes 56.

FIGS. 6A-6D illustrate multiple views of the base portion 18 according to some embodiments. FIG. 6A is a top view and FIG. 6B is a side cross-sectional view of the base portion 18. As illustrated, the outlet 34 can be positioned at the center of the base portion and may be formed separately and bonded to the base portion 18, or may be formed as an integral part of the base portion. FIG. 6C illustrates a detailed view of the outlet 34, including two optional barbs 58 for securing an outlet line. FIG. 6D shows a detailed view of an edge of the base portion 18, including a tongue-and-groove configuration for coupling with the support element 22, as shown in more detail in FIG. 3D.

Figure 7A:
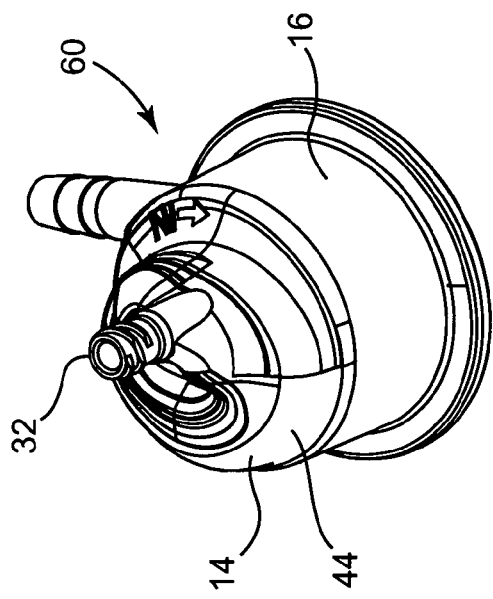
FIG. 7A is a perspective view of a top portion of an arterial filter according to an embodiment of the present invention.
Figure 7C:
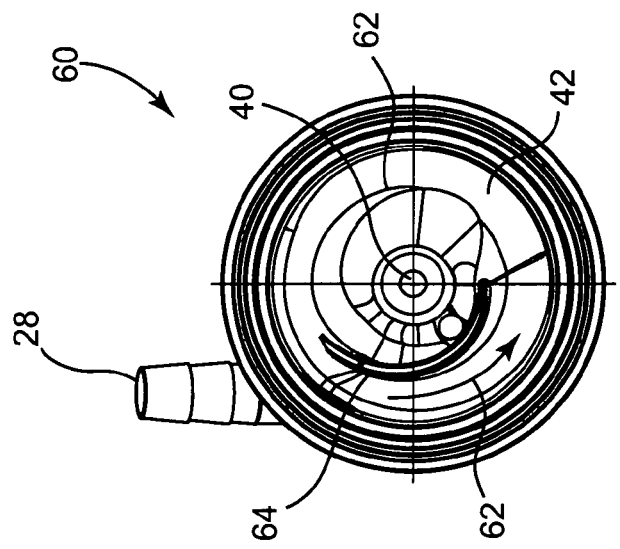
FIG. 7C is a bottom view of the top portion of FIG. 7A.
Figure 7B:
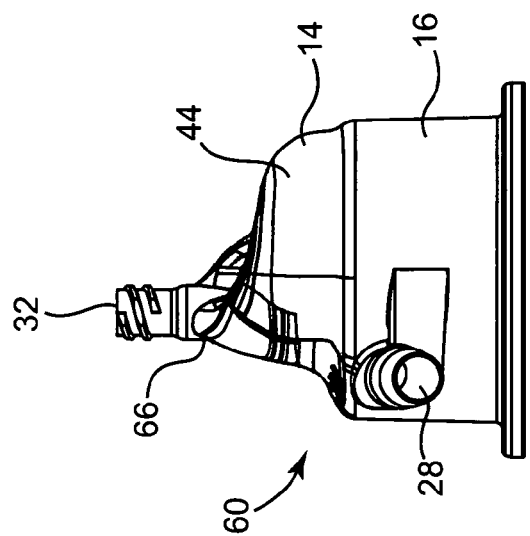
FIG. 7B is a side elevation view of the top portion of FIG. 7A.

FIGS. 7A-7C show additional views of a top portion 60 of the housing 12, comprising the cap portion 14 and the wall portion 16 coupled together as an integral whole. As discussed briefly with reference to FIGS. 3A-3C, in some embodiments the inner surface 42 of the cap portion 14 is contoured to improve gross air handling of gaseous microemboli (e.g., air bubbles) within the inlet chamber 24. For example, in the embodiment depicted in FIGS. 7A-7C, the inner surface 42 of the cap portion 14 slopes upwardly around the longitudinal axis of the housing (e.g., the location of the volume displacer 40) in an inwardly spiraled fashion towards the vent 32. The outer surface 44 may generally follow the contour of the inner surface 42, although this is not required.

The contoured inner surface 42 defines a blood flow path 62 for blood circulating through the upper portion of the inlet chamber 24 that facilitates the venting of gaseous microemboli. A flow director 64 can guide at least a portion of blood incoming from the inlet 28 around the perimeter of the cap portion 14 after which it spirals more tightly towards the vent 32. For example, the flow director 64 can separate blood initially flowing in from the inlet 28 from blood that has already circled around the inlet chamber 24. Advantageously, the flow director 64 can prevent gaseous microemboli which are rising to the vent 32 from mixing with blood entering through the inlet 28. This can prevent the high velocity inlet blood flow from breaking up and/or entraining the gaseous microemboli.

As blood flows through the inlet chamber 24, gaseous microemboli tend to rise through the blood towards the vent 32 due to inherent buoyancy of the gaseous matter. As blood is guided upward toward the vent 32 by the blood flow path 62, the upward velocity component of the blood flow adds to the natural buoyancy of the gaseous microemboli to facilitate their rise through the blood to the inner surface 42 of the cap portion 14. The upward and inward flow path 62 along the inner surface 42 carries the gaseous microemboli around the spiral to the vent 32 where they can escape the blood flow through the vent.

In some embodiments, the inner surface 42 is contoured to provide an elevated region 66 adjacent the vent 32. In some cases without such an elevated region, a horizontal velocity component of the blood flow may carry the gaseous microemboli past the vent 32 before the upward force on the gaseous microemboli moves them out of the blood flow into the vent 32. The elevated region 66 creates an area above the blood flow path 62 that is protected, to varying degrees, from high velocity blood flow, which allows the gaseous microemboli to rise out of the blood as it passes under the vent 32.

In some embodiments, the inner surface 42 of the cap portion 14 is configured to limit or eliminate the trapping or immobilization of gaseous microemboli (e.g., air bubbles) within the inlet chamber. For example, the generally spiraled contour of the inner surface 42 can promote the movement of gaseous microemboli towards the vent 32. Immobilization of gaseous microemboli presents an undesirable situation in which the gaseous microemboli may eventually be swept by the circulating blood towards the filter element 20. According to some embodiments, configurations of the inner surface 42 minimize the presence of stagnant flow regions during operation at low flow rates (e.g., less than about 1 liter per minute), or recirculation zones during operation at higher flow rates, while providing sufficient upward slope to facilitate venting of gaseous microemboli.

FIG. 8A illustrates the inner and the outer surfaces 42, 44 as opposing surfaces of the cap portion 14, while FIG. 8B illustrates only the inner surface 42 without the outer surface 44 to more clearly show the form of the inner surface 42 from above. FIGS. 8A and 8B also show the top portion 60 in partial cross-section, including an additional feature that can limit or eliminate stagnant flow and/or recirculation zones along the inner surface 42 of the cap portion 14 according to one preferred embodiment. As is shown, the cap portion 14 can be contoured to include a projection 68 extending down from the inner surface 42 and into the blood flow path 62 past the vent 32. According to one embodiment, the projection 68 creates a blood flow that minimizes the opportunity for the immobilization of gaseous microemboli.

As shown in FIGS. 8A and 8B, the projection 68 is located along the blood flow path 62 past the vent 32, so that the inner surface 42 guides blood around the inlet chamber 24 and up past the elevated region 66 and vent 32, and then back down against the projection 68 into the circulating blood flow. The projection 68 promotes movement of gaseous microemboli by creating a local minima in the contour of the inner surface 42. Gaseous microemboli pushed against the projection 68 by circulating blood tend to either travel directly up to the vent 32 in a clockwise direction (with respect to a bottom view), against the blood flowing back down from the vent 32, or travel with the blood as it spirals in a counterclockwise direction (with respect to a bottom view) towards the vent 32. According to one embodiment, when gaseous microemboli are carried by the blood flow past the vent 32, the horizontal velocity of the blood flow (and the entrained microemboli) tends to decrease as it hits the projection 68. With a decreased horizontal velocity, the natural buoyancy of the gaseous microemboli urges them up through the blood flow towards the vent 32.

Figure 9:
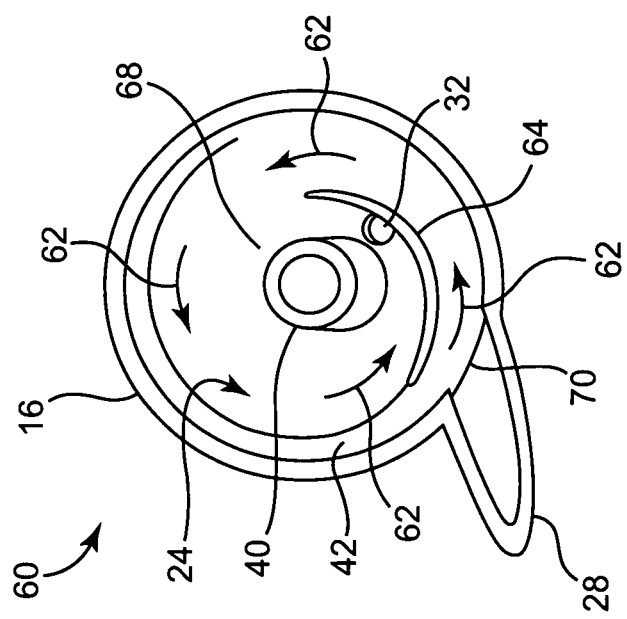
FIG. 9 is a partial cross-sectional, partial perspective bottom view of the top portion of FIG. 7A according to an embodiment of the present invention.

Referring to FIG. 9, an enlarged bottom view of the top portion 60 similar to FIG. 7C is shown in partial cross section according to one embodiment of the invention. A sectional view of the inlet 28 is shown, including an opening 70 of the inlet into the inlet chamber 24. As blood enters the inlet chamber, a portion of it can flow up against the inner surface 42 along the flow path 62 until it is guided under the vent 32 by the flow director 64. After passing the vent 32, the blood flow is directed down by the projection 68, while gaseous microemboli can float up towards the vent 32 as previously discussed.

Figure 10:
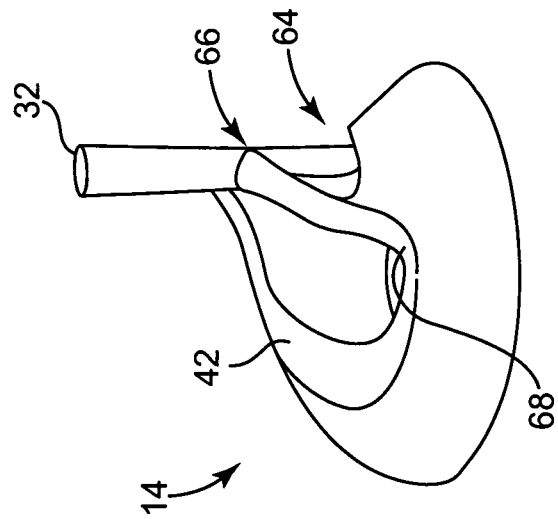
FIG. 10 is a partial perspective view of the top portion of FIG. 7A according to an embodiment of the present invention.

Referring to FIG. 10, a perspective view of the cap portion 14 is shown, illustrating only the inner surface 42 without the outer surface 44 to more clearly show the form of the inner surface 42 from above. As is shown, the projection 68 presents a local minima in the inner surface 42 between a high point of the blood flow path proximate the vent 32 and the portion of the blood flow path spiraling towards the vent 32. As such, in one embodiment the projection 68 eliminates any level regions of the inner surface 42 where gaseous microemboli may become immobilized.

Figure 11B:
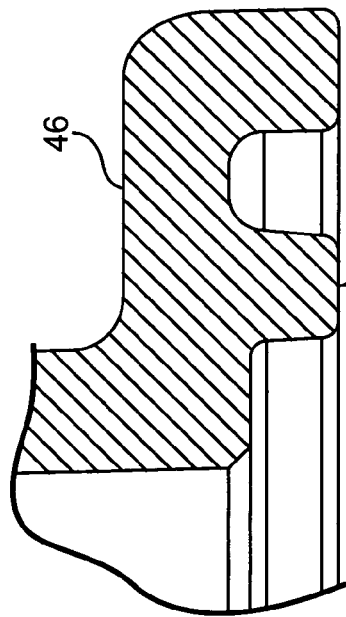
FIG. 11B is a detailed view of a coupling flange of the top portion of FIG. 11A according to an embodiment of the present invention.
Figure 11D:
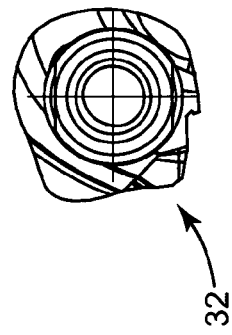
FIG. 11D is a top detailed view of a vent of top portion of FIG. 11A according to an embodiment of the present invention.
Figure 11A:
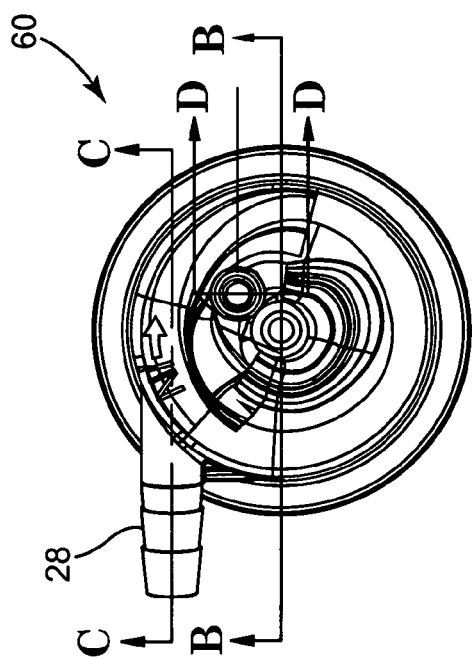
FIG. 11A is a top view of a top portion of an arterial filter according to an embodiment of the present invention.
Figure 11C:
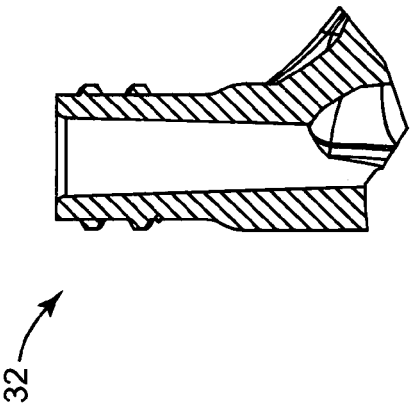
FIG. 11C is a cross-sectional view of the top portion of FIG. 11A along line DD according to an embodiment of the present invention.
Figure 11E:
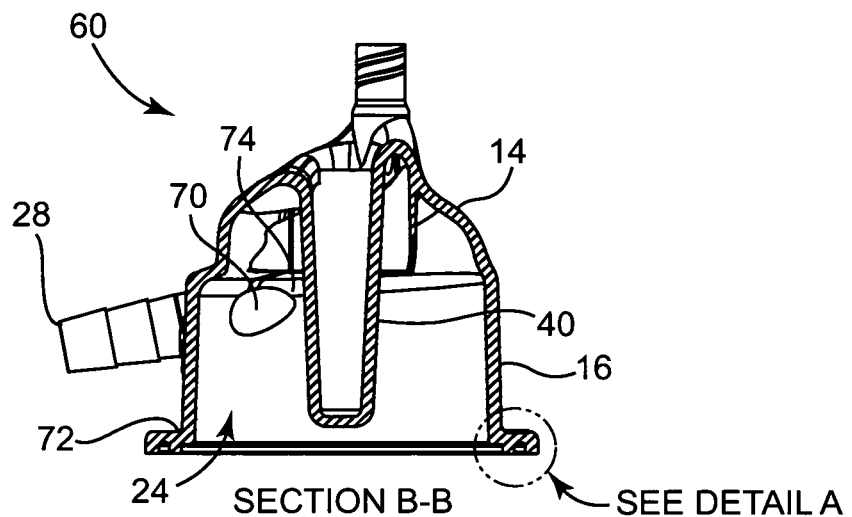
FIG. 11E is a cross-sectional view of the top portion of FIG. 11A along line BB according to an embodiment of the present invention.

FIGS. 11A-11F show additional views of the top portion 60 of the housing 12, comprising the cap portion 14 and the wall portion 16 coupled together according to one embodiment. FIG. 11A is a top view of the top portion 60, while FIGS. 11C and 11D illustrate cross-sectional and top views, respectively, of the vent 32. FIG. 11B illustrates a detailed view of the coupling flange 46 of the wall portion 16, which is also shown in FIGS. 3C, 3D and 11E.

Figure 11F:
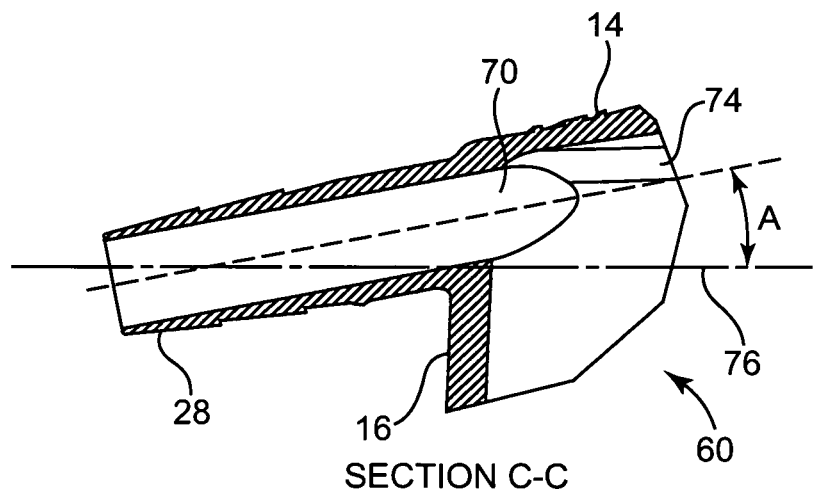
FIG. 11F is a cross-sectional view of the top portion of FIG. 11A along line CC according to an embodiment of the present invention.

Turning now to FIGS. 11E and 11F, the inlet 28 is displaced with respect to the top portion 60 in order to facilitate blood circulation throughout the blood filter according to some embodiments. As previously mentioned, it is desirable to decrease the pressure drop across an arterial blood filter in order to decrease the overall extracorporeal blood circuit pressure and thus avoid trauma to the circulating blood. In cases where blood filters are designed for use with an adult-sized patient, the design often includes a large volume inlet chamber, compared to the inlet of the filter, to diffuse the blood flow, in order to decrease its velocity as it enters the filter. As the size of the filter decreases (e.g., a pediatric filter), however, less room is available to diffuse the blood, especially when blood is initially directed towards a restricted upper area leading to a filter vent. For example, with reference to FIG. 11E, the cap portion 14 of the depicted filter narrows upward towards the vent 32 in order to direct blood past the vent 32. In a case where blood initially enters the filter through the cap portion 14, the reduced volume of the cap portion 14 could create a faster than desired blood flow.

According to one embodiment, the inlet 28 is spaced apart from the cap portion 14 in order to provide a larger volume by utilizing the space immediately adjacent the inlet opening 70. For example, the inlet 28 may be coupled to the wall portion 16 at a point between the cap portion 14 and a lower edge 72 of the wall portion 16. By positioning the inlet 28 in this area, the larger volume of the inlet chamber 24 adjacent the wall portion diffuses and decreases the velocity of the blood as it exits the inlet 28 to a greater extent than if blood directly entered the smaller volume of the cap portion 14. As shown in FIG. 11E, in one embodiment, the opening 64 of the inlet is proximate the cap portion 14, e.g., proximate the junction 74 between the wall portion 16 and the cap portion 14.

In addition, placement of the inlet 28 along the wall portion 16 of the filter can lead to a more evenly distributed blood flow according to some embodiments. For example, because of the inlet's lower position along the filter housing, blood passes from the inlet 28 into the inlet chamber 24, and radially disperses outward from the opening 70. Referring to FIGS. 11E and 3C, some blood flows generally straight outward from the opening 70, some blood can impact against the filter element 20, some blood flows downward along the wall portion 16 between the filter element 20 and the wall portion 16, and some blood flows upward toward the cap portion 14. Thus, there tends to be an even distribution of blood throughout the inlet chamber 24 at a decreased velocity and the blood tends to evenly distribute over the pleats of the filter element, which can promote the operation of and reduce the pressure drop across the filter.

As blood is introduced into the inlet chamber, it starts to circulate as it is guided by the curved wall portion 16. In some cases the circulation may remain around the perimeter of the inlet chamber, creating an uneven distribution of blood across the filter element. Referring back to FIG. 9, in some embodiments the inlet 28 is coupled to the wall portion in a non-tangential orientation to advantageously affect the blood circulation within the inlet chamber. Because of the non-tangential flow path, some blood hits the filter element, some blood hits the wall portion 16 at an angle and some blood is directed towards the volume displacer 40, rather than all of the blood being swept away by the curving wall portion. Thus, the non-tangential orientation of the inlet 28 can promote a more evenly distributed blood flow. By utilizing the entire inlet chamber for blood flow, the filter is able to function at a reduced blood volume needed, for example, for pediatric patients, while maintaining a disproportionately high flow rate and avoiding an elevated pressure drop.

To facilitate the venting of gaseous microemboli, the blood can be directed against the inner surface 42 of the cap portion 14, which guides the blood in a spiraling blood flow path to the vent 32. In the case where the inlet 28 is not coupled directly to the cap portion 14, the inlet 28 can be angled upward with respect to the filter in order to introduce a vertical velocity component into the blood flow to direct at least a part of the blood towards the cap portion and vent. Referring to FIG. 11F, according to one embodiment, the inlet 28 is coupled to the wall portion 16 and is angled at an upward angle A with respect to a horizontal plane 76 taken through the top portion 60. In one embodiment, angle A is approximately 10.6°, although A may be approximately 10° or between approximately 7° and approximately 13°. Of course other upward angles A below 7° and above 13° may also be used depending upon a particular application.

In use, the path followed by blood from the inlet 28 is best described with reference to FIGS. 3C, 7C, 9 and 10. After entering through the inlet 28, the blood generally disperses throughout the inlet chamber 24 as previously described and some of the blood is directed by the shape of the wall portion 16 and the inner surface of the cap portion 14. At least some blood is guided by the inner surface 42 of the cap portion 14, including the flow director 64, in an inward spiral, wherein the tightness of the spiral increases along the flow path 62 as the blood is directed around the volume displacer 40 inwardly towards the center of the blood filter. The blood then generally circles around the inlet chamber 24 in a counter-clockwise direction, but follows no particularly defined path.

As the blood follows its path around the top portion 60 of the housing and through the filter, gaseous microemboli rise to the top of the housing and are urged upward toward the vent 32 by the inner surface 42 of the cap portion 14. The slight upward tilt on the inlet port 28 helps in this process. The inward flow path of blood carries the gaseous microemboli around the spiral to the elevated region 66 near the vent 32 where they rise to the top and collect for venting. The projection 68 extending from the inner surface 42 facilitates movement of the gaseous microemboli as previously discussed. As the blood continues its flow at a decreased velocity around the inlet chamber 24, some blood begins to flow downward into the filter element 20. As previously mentioned, the decreased blood velocity tends to promote an even distribution of blood over the filter element 20. The blood then passes through the filter element into the outlet chamber 26 and downward through the outlet 34. From there, it exits the blood filter where it may be delivered to a patient through a patient return line.

In use, the blood filter according to embodiments of the invention is a component of an arterial blood filtration system. For example, in the case of cardiopulmonary bypass (CPB), blood from the patient flows into a reservoir from which it is pumped through the rest of the CPB perfusion circuit using a pump. From the pump the blood flows through a heat exchanger and oxygenator, where carbon dioxide is removed and the blood is oxygenated. Prior to returning the blood to the patient, it is perfused through the blood filter to filter off particulate and gaseous emboli. Methods of using the arterial blood filter according to embodiments of the invention comprise providing the arterial blood filter for filtration of microemboli from the blood during an operative procedure which includes oxygenation of the blood, priming the filter as described above, and connecting the filter to the patient's circulatory system. In alternative embodiments, the blood filter can be used in other procedures using an extra corporeal perfusion circuit that incorporates blood filtering.

Thus, embodiments of the ARTERIAL BLOOD FILTER and methods of using the same are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A blood filter comprising:
 a housing comprising a cap portion, a base portion, and a generally cylindrical wall portion between the cap portion and the base portion, the housing defining a longitudinal axis and the wall portion forming an inner surface having a curved region that defines a radius of curvature about the longitudinal axis in a transverse plane perpendicular to the longitudinal axis;
 a filter element disposed within the housing and dividing the housing into an inlet chamber and an outlet chamber;
 a support element fixedly connected to the housing for supporting the filter element such that the filter element terminates at a filter tip opposite the base portion;
 an inlet terminating at, and fluidly open relative to, an opening in the curved region of the inner surface of the generally cylindrical wall portion, wherein the inlet is positioned at an upward angle with respect to the housing;
 a projection extending downwardly within an interior of the cap portion, the projection radially spaced a first distance from the longitudinal axis, wherein the opening for the inlet is radially spaced a second distance from the longitudinal axis, the first distance being less than the second distance,
 wherein the opening is in fluid communication with the inlet chamber,
 wherein relative to a direction of the longitudinal axis, at least a portion of the inlet opening is spatially between the filter tip and the base portion,
 and further wherein the inlet is positioned to disperse incoming blood throughout the inlet chamber; and
 an outlet in fluid communication with the outlet chamber.

2. The blood filter of claim 1, wherein the opening in the generally cylindrical wall portion is proximate the cap portion.

3. The blood filter of claim 1, wherein the inlet is positioned to direct at least a portion of the incoming blood towards the cap portion.

4. The blood filter of claim 1, wherein the upward angle is between approximately 7 and approximately 13 degrees with respect to a horizontal plane intersecting the housing.

5. The blood filter of claim 4, wherein the upward angle is approximately 10 degrees with respect to the horizontal plane intersecting the housing.

6. The blood filter of claim 4, wherein the upward angle is approximately 10.6 degrees with respect to the horizontal plane intersecting the housing.

7. The blood filter of claim 1, wherein the housing has a prime volume configured for use with pediatric patients.

8. The blood filter of claim 7, wherein the prime volume is approximately 40 milliliters.

9. The blood filter of claim 1, wherein the cap portion comprises a vent and the projection proximate the vent, the projection configured to limit immobilization of gaseous microemboli within the inlet chamber.

10. The blood filter of claim 1, wherein the inlet is coupled to the wall portion in a non-tangential orientation relative to a curvature of the curved region of the wall portion at which the opening is formed.

11. A blood filter comprising:
 a housing comprising a base portion, a generally cylindrical wall portion coupled with the base portion, and a cap portion coupled with the generally cylindrical wall portion, wherein the cap portion comprises an upwardly sloping inner surface;
 a filter element disposed within the housing and dividing the housing into an inlet chamber and an outlet chamber;
 a support element fixedly connected to the housing for supporting the filter element;
 an inlet in fluid communication with the inlet chamber;
 an outlet in fluid communication with the outlet chamber;
 a vent in the cap portion;
 wherein the cap portion defines a spiral blood flow path from the inlet to and past the vent;
 a projection extending downwardly from the inner surface proximate the vent configured to limit immobilization of gaseous microemboli within the inlet chamber, the projection creating a local minima in a contour of the inner surface proximate the vent; and
 a flow director extending downwardly from the inner surface for guiding blood flow from the inlet toward the vent;
 wherein relative to a direction of the blood flow path from the inlet, the projection is located downstream of the vent such that blood flow from the inlet passes the vent before contacting the projection, and
 wherein the projection is spaced radially inward relative to the inlet; and
 is radially asymmetric relative to the center longitudinal axis of the generally cylindrical wall portion.

12. The blood filter of claim 11, wherein the upwardly sloping inner surface defines the blood flow path for guiding blood past the vent, and wherein the projection is located along the blood flow path subsequent to the vent.

13. The blood filter of claim 11, wherein the inner surface provides an upwardly and inwardly spiraling blood flow path.

14. The blood filter of claim 13, wherein the vent is offset and positioned at a highest part of the cap portion.

15. The blood filter of claim 11, wherein the inlet is positioned at an upward angle with respect to the housing.

16. The blood filter of claim 15, wherein the inlet comprises an opening in the generally cylindrical wall portion.

17. The blood filter of claim 16, wherein the opening is proximate the cap portion.

18. The blood filter of claim 11, wherein the projection is defined by a leading face facing the vent and a trailing face opposite the leading face, the leading and trailing faces extending from the inner surface and intersecting at terminal end of the projection, and further wherein the leading face projects radially outwardly in extension from the inner surface to the terminal end and the trailing face defines a convex curve in extension from the terminal end to the inner surface.

19. The blood filter of claim 11, wherein relative to an upright orientation of the blood filter, the inner surface extends above the projection immediately upstream and immediately downstream of the projection along a downwardly sloping shape of the inner surface downstream from the vent.

* * * * *